US012357773B2

(12) United States Patent
Alan et al.

(10) Patent No.: US 12,357,773 B2
(45) Date of Patent: Jul. 15, 2025

(54) NEBULIZER

(71) Applicant: Monash University, Clayton (AU)

(72) Inventors: Tuncay Alan, Clayton (AU); Adrian Neild, Clayton (AU); Nguyen Hoai An Le, Clayton (AU); Jason Brenker, Clayton (AU)

(73) Assignee: Monash University, Clayton Victoria (AU)

( * ) Notice: Subject to any disclaimer, the term of this patent is extended or adjusted under 35 U.S.C. 154(b) by 1152 days.

(21) Appl. No.: 17/262,612

(22) PCT Filed: Jul. 24, 2019

(86) PCT No.: PCT/AU2019/050778
§ 371 (c)(1),
(2) Date: Jan. 22, 2021

(87) PCT Pub. No.: WO2020/019030
PCT Pub. Date: Jan. 30, 2020

(65) Prior Publication Data
US 2021/0268209 A1    Sep. 2, 2021

(30) Foreign Application Priority Data
Jul. 24, 2018 (AU) ................................ 2018902671

(51) Int. Cl.
*A61M 11/00* (2006.01)
*B05B 17/06* (2006.01)

(52) U.S. Cl.
CPC ......... *A61M 11/005* (2013.01); *A61M 11/001* (2014.02); *B05B 17/0607* (2013.01);
(Continued)

(58) Field of Classification Search
CPC .............. A61M 11/005; A61M 11/001; A61M 2205/02; A61M 2205/0244; A61M 11/00;
(Continued)

(56) References Cited

U.S. PATENT DOCUMENTS 3,561,444 A * 2/1971 Boucher .............. A61M 11/005
                                                        261/DIG. 65
3,861,386 A * 1/1975 Harris ................. B05B 17/0615
                                                        239/338

(Continued)

FOREIGN PATENT DOCUMENTS

EP    0923957 A1    6/1999
JP    07-328503 A    12/1995
(Continued)

OTHER PUBLICATIONS

Extended European Search Report received for European Patent Application No. 19841650.5, mailed on Mar. 18, 2022, 9 pages.
(Continued)

*Primary Examiner* — Timothy A Stanis
(74) *Attorney, Agent, or Firm* — Shook, Hardy & Bacon L.L.P.

(57) ABSTRACT

A nebulizer (10) having a housing which includes a chamber that has an outlet to the chamber for the egress of atomised fluid particles from within the chamber. The nebulizer (10) further includes a solid substrate (11) within the chamber of the housing. A linear channel (12) is formed in the substrate (11) that has a closed base, opposite side walls and an opening that opens through an upper surface of the substrate (11). A vibration generator (17) is attached to the substrate (11) at a position spaced from the channel (12) for generating high frequency vibration that transmits through the
(Continued)

substrate (11) to the channel (12) to atomise fluid within the channel (12). A feeding facility (15) is provided for feeding fluid to the channel (12).

18 Claims, 4 Drawing Sheets

(52) U.S. Cl.
CPC ...... *B05B 17/0615* (2013.01); *B05B 17/0669* (2013.01); *A61M 2205/02* (2013.01); *A61M 2205/0244* (2013.01); *B05B 17/06* (2013.01)

(58) Field of Classification Search
CPC .. A61M 2205/0238; A61M 2205/0294; A61M 2202/0007; A61M 2202/04; A61M 2209/045; A61M 2210/1025; B05B 17/0607; B05B 17/0615; B05B 17/0669; B05B 17/06; B05B 17/00; B05B 17/0676; B05B 17/0684; B05B 17/0623
USPC ........ 128/200.16; 239/102.1–102.2; 222/590
See application file for complete search history.

(56) References Cited

U.S. PATENT DOCUMENTS 4,976,259 A * 12/1990 Higson ............. A61M 15/0085 239/102.1
6,247,525 B1 * 6/2001 Smith ................... B05B 7/0012 165/104.34
6,405,934 B1 * 6/2002 Hess ................. A61M 15/0085 128/200.14
7,708,943 B1 * 5/2010 Robinson ............. G01N 33/225 422/89
8,439,280 B2 * 5/2013 Marchetti ........... B05B 17/0646 239/326
8,967,493 B2 * 3/2015 Kohnle ................ A61M 11/005 239/102.1
9,358,568 B2 * 6/2016 Tabata ................ B05B 17/0623
10,154,923 B2 * 12/2018 Hunter .................. A61F 9/0008
2003/0080214 A1 * 5/2003 Hess ................... B05B 17/0646 239/428.5
2004/0124173 A1 * 7/2004 Hess .................... A61M 11/005 216/27
2007/0158459 A1 7/2007 Aval et al.
2008/0142010 A1 * 6/2008 Weaver ................ A61M 11/001 128/203.29
2008/0217430 A1 * 9/2008 Feriani ................ B05B 17/0646 239/102.1
2011/0066108 A1 * 3/2011 Geipel .............. A61M 5/16877 137/557
2013/0107267 A1 * 5/2013 Leuenberger ..... A61M 5/16831 356/445
2015/0165466 A1 * 6/2015 Hammer ............. B05B 17/0661 239/102.2
2017/0178884 A1 * 6/2017 Murtazin ................ G01J 3/443
2017/0280771 A1 * 10/2017 Courbat .............. B05B 17/0661
2017/0333644 A1 * 11/2017 Reboud ............... B05B 17/0607
2021/0022406 A1 * 1/2021 Minami .............. B05B 17/0607

FOREIGN PATENT DOCUMENTS

| | | | |
|---|---|---|---|
| JP | H 07328503 | | * 12/1995 |
| JP | 2739533 | B2 | 4/1998 |
| JP | 2004226365 | A | 8/2004 |
| JP | 2008-104974 | A | 5/2008 |
| JP | 2009-154058 | A | 7/2009 |
| JP | 2012148256 | A | 8/2012 |
| JP | 7043304 | B2 | 3/2022 |
| WO | 2012026963 | A3 | 3/2012 |

OTHER PUBLICATIONS

International Search Report in related application PCT/AU2019/050778, mailed Sep. 18, 2019, 3 pages.

* cited by examiner

NEBULIZER

CROSS-REFERENCE TO RELATED APPLICATIONS

This application claims priority under 35 U.S.C. § 365 to PCT/AU2019/050778, filed on Jul. 24, 2019, entitled "NEBULIZER," which claims priority to Australian App. No. 2018902671, filed on Jul. 24, 2018. The entirety of the aforementioned applications are hereby incorporated by reference herein.

TECHNICAL FIELD

The present invention relates to a nebulizer that is capable of generating very small droplets for use in various fields such as thin film deposition, pulmonary drug delivery and mass spectrometry. It is expected that other fields will have use for the nebulizer of the invention.

BACKGROUND OF INVENTION

The discussion of the background to the invention that follows is intended to facilitate an understanding of the invention. However, it should be appreciated that the discussion is not an acknowledgement or admission that any aspect of the discussion was part of the common general knowledge as at the priority date of the application.

Various different forms or nebulizers exist already and fall generally into four different groups, comprising 1) Jet nebulizers, 2) Ultrasonic nebulizers, 3) Mesh nebulizers and 4) Surface Acoustic Wave atomizers. These are discussed separately below.

Jet Nebulizers

Jet nebulizers rely on a source of constant gas flow from either a compressor or central compressive gas supply to push a liquid dose through a small aperture to generate small aerosol droplets. Jet nebulizers are advantageously relatively cheap and of low complexity, but disadvantageously, they have low efficiency and require the separate gas source. In respect of efficiency and using the example of pulmonary drug delivery, less than 10% of the droplets created by a Jet nebulizer will be fit for inhalation delivery. The remaining droplets are recycled in a liquid reservoir that forms part of the nebulizer. The recycled liquid is available for return to the aperture for the next use of the nebulizer.

An improved nebulizer would dispense with the need for a compressor or central compressive gas supply and would have increased efficiency in terms of useful droplet generation.

Ultrasonic Nebulizer

Ultrasonic nebulizers employ a piezoelectric (PZT) material to vibrate a liquid and generate droplets from it. There are two different arrangements that are usually employed in which in the first arrangement, the PZT is placed in direct contact with the liquid to be atomised and in the second arrangement, a liquid medium is positioned between the PZT and the liquid to be atomised and the respective liquids are separated by a membrane. Both of these arrangements are inefficient in only producing small quantities of usable atomised droplets so that both of these arrangements still require a recycling facility for the larger droplets to be accumulated for subsequent further atomisation.

Further disadvantages with this form of nebulizer are that it cannot aerosolise viscous solutions, while the liquid to be atomised is exposed heat generated by the PZT as a result of the close proximity of the PZT to the liquid, particularly in the first arrangement where there is direct contact between the PZT and the liquid. That exposure can result in degradation of liquids that are heat-sensitive. A still further disadvantage with this form of nebulizer is that the amount of liquid that can be atomised is smaller than the initial volume that is provided to the nebulizer, which results in a residual volume of liquid following completion of atomisation.

An improved nebulizer would have a reduced residual volume of liquid and reduced application of heat to the liquid being atomised.

Mesh Nebulizer

Mesh nebulizers have been developed more recently and provide, in the view of the inventor, the most advanced current approach in liquid atomization technology. Mesh nebulizers employ a porous mesh through which a liquid is passed to form very small droplets. A typical mesh has thousands of very small pores with the pore size dictating the droplet size that is produced. The pores can be conical so that a wide inlet is provided which narrows to a narrow outlet.

Mesh nebulizers are categorised into two major groups, being static mesh and vibrating mesh. There is a simple difference between the two forms of mesh nebulizer and that is in the positioning of the PZT actuator of these devices. In a vibrating mesh nebulizer, the PZT actuator is placed in direct contact with the mesh, whereas in a static mesh nebulizer, the PZT actuator is positioned spaced from the mesh.

A drawback with the mesh nebulizer devices is that the mesh component is expensive given the large number of very small pores required and is thus not realistically disposable (because of the expense). This makes the overall device expensive. In addition, daily or weekly cleaning is necessary to prevent the small pores from becoming blocked, such as from crystallisation of the samples being atomised. Even with regular cleaning, the mesh component typically needs to be replaced every six months.

Surface Acoustic Wave Nebulizer

Surface acoustic wave (SAW) nebulizers utilize a PZT substrate to excite a liquid sample and to atomize droplets via capillary wave breakup.

SAW nebulizers can advantageously control the size of the droplets produced, but disadvantageously they operate at low throughputs and can cause excessive heating of the samples to be atomised.

The present invention is intended to provide a nebulizer that overcomes drawbacks or difficulties associated with the prior art, including but not limited to the drawbacks or difficulties associated with the prior art discussed above.

SUMMARY OF INVENTION

According to the present invention there is provided a nebulizer comprising:

a. a housing defining a chamber and having an outlet to the chamber for the egress of atomised fluid particles from within the chamber,
b. a solid substrate within the chamber of the housing,
c. a linear channel formed in the substrate that has a closed base, opposite side walls and an opening that opens through an upper surface of the substrate,
d. a vibration generator attached to the substrate at a position spaced from the channel for generating high frequency vibration that transmits through the substrate to the channel to atomise fluid within the channel,
e. a feeding facility for feeding fluid to the channel.

A nebulizer according to the invention employs a channel as the receptacle in which fluid to be atomised is contained. This distinguishes the invention from prior art nebulizers which provide fluid as a large body that is progressively atomised. In contrast, in a nebulizer according to the invention, fluid is fed or drawn into a channel and only that fluid within the channel is subject to atomisation by the high frequency vibration that is generated by the vibration generator and that transmits through the substrate to the channel. The forms of each of the prior art nebulizers discussed as prior art herein as known to the inventor employ a large body of liquid that is atomised from that large body. Those nebulizers do not feed a channel from a body of liquid. The feed can, for example, be by capillary action upon excitation of the substrate by the vibration generator.

Testing of nebulizers according to the invention has established that the variation in droplet size of the droplets that are produced can be controlled or tuned so that the level of variability is very low and the consistency is very good. In some forms of the invention, the size of the particles can be tuned on-demand by changing the frequency of actuation of the vibration generator. This has advantageous outcomes for aerosol drug delivery into the lungs for example, as the size of delivered droplets determines where in the lung the droplets are deposited as well as influencing the therapeutic effectiveness of the drug.

From measurements of the droplet size relative to the driving frequency of the high frequency vibration, as well as imagery that has been observed of the fluid/air interface, the physical mechanism of the atomising effect of nebulizers according to the invention is considered to involve capillary waves forming at the fluid/air interface at the top or opening of the channel or channels formed in the substrate. The periodicity of this interface is set by the driving frequency. This in turn regulates the size of droplets produced. Thus by using a vibration generator such as a piezoelectric actuator which is capable of exciting at or to a range of or various frequencies, different sizes of droplets can be produced from the same nebulizer. Physical properties affecting capillary wavelength at the fluid/air interface include 1) the density of the two fluids in contact, 2) the surface tension and 3) the driving wavelength.

A nebulizer according to the invention can employ a linear channel of any suitable form or geometry. Advantageous results have been achieved with a channel having a high aspect ratio in which the depth of the channel is much greater than the width. Examples of channels that are expected to be suitable for use in the invention and that have a high aspect ratio, include channels in which the aspect ratio ranges from 7:1 to 15:1. It should be appreciated however that the aspect ratio is not limited to this range and greater or lesser aspect ratios could be employed. Indeed, channels having a low aspect ratio could also be employed, but testing to date has been in respect of high aspect ratio channels and these have provided highly advantageous results.

The linear channel that is employed in the invention can be a microscopic channel consistent with the requirement to generate microscopic particles. In some forms of the invention, the opening of the channel through the upper surface of the substrate has a width transverse to the length of about 1.5 micrometres. In other forms of the invention, the opening of the channel can have a width of about 20 micrometres. Other widths that have been employed in testing to date include 3, 5 and 10 micrometres. Where the channel that is employed is a high aspect ratio channel, the depth of the channel can thus be from 10.5 micrometres for a channel that has an aspect ratio of 7:1 and a channel opening of 1.5 micrometres and up to a 300 micrometre depth for a channel that has aspect ratio of 15:1 and a channel opening of 20 micrometres.

The linear channel that is employed in the invention can be formed in any suitable manner. Because it will normally be formed in microscopic dimensions, not all ordinary fabrication methods will be available. Early prototypes have employed etching technology, in particular deep reactive ion etching to form the channel.

The substrate can be formed from any suitable material. The substrate is a solid substrate and is preferably a rigid substrate. Early prototypes have employed a substrate formed from silicon which is readily available, cheap, easily fabricated and advantageously, is inert to most biological and chemical components. Moreover, because silicon is cheap and readily fabricated to form the linear channel, a further benefit of the use of silicon for the substrate is that the substrate can be disposable. The main benefit of this is that the use of a disposable substrate eliminates the need for the substrate to be cleaned and/or sterilised between uses. Cleaning is required in prior art nebulizers mainly to clear clogged or blocked pores through which atomisation of liquid takes place, while sterilisation is required to prevent contamination of one liquid by the next. The absence of pores in the present invention is considered to provide significant advantages over the prior art.

Alternative materials for the substrate include glass, fused silica and Lithium Niobate for example.

The surface of the channel can be treated if required and depending on the type of fluid to be atomised. In some forms of the invention, the surface of the channel can be treated to render it hydrophilic. That surface treatment can be achieved in a silicon substrate by the application of $O_2$ plasma to the channel surface. Other forms of surface treatment however could be employed, particularly if the substrate is other than silicon.

A single linear channel can be formed in the substrate, or multiple channels can be formed. The use of multiple channels enables the output of the nebulizer according to the invention to be increased. Where multiple channels are formed, these can be formed in a parallel array. Two channels can be formed parallel to each other or three or more channels can be formed in parallel formation. Alternatively, the two or more channels can be formed other than in a parallel formation and could, for example be formed perpendicular to each other, such as in a T or L formation for two channels, and in a C or square/rectangular formation for three or four channels. Other formations and other numbers of channels can be employed. Equally, where multiple channels are employed, the respective channels can be of the same dimensions or of different dimensions. The dimensions of the respective channels might differ as a result of their different proximity and/or orientation relative to the vibration generator.

The vibration generator can have any suitable form however in current forms of the invention, the vibration generator is a piezoelectric actuator that employs a rectangular piezoelectric block that is actuated or excited electrically. The use of a piezoelectric actuator permits nebulizers according to the invention to have a very small footprint while also allowing the vibrations that are generated in the solid substrate to have a high frequency. Early prototypes have generated actuation vibrations in a frequency range from 1.5 to 4.2 MHz, although the expected frequency range is from about 0.5 to 5 MHz. Even higher frequencies, such as in the range of 5 to 20 MHz or even much higher, could be generated and would be expected to provide beneficial results.

A vibration generator can be placed on the upper surface of the substrate through which the channel or channels open. The vibration generator can be spaced from the channel or channels any suitable distance. The distance can be selected to ensure that heating of the fluid being atomised by the vibration generator is minimised or is negligible. Also, the vibration generator can be pulsed on and off rather than being left on continuously to further limit heat transfer to the fluid being atomised. This distinguishes a nebulizer according to the invention from some of the prior art discussed herein in which heating of the fluid being atomised is a problem or disadvantage.

In early prototypes, a single linear channel has extended across the substrate and the vibration generator, in the form of a rectangular piezoelectric block, has been positioned to generate high frequency vibrations that transmit through the substrate. In these early prototypes, the vibrations have mainly transmitted through the substrate perpendicular to the channel, however parallel transmission can also be employed.

In alternative arrangements, the vibration generator can be placed on the lower or underneath surface of the substrate opposite to which the channel or channels open. In one particular form of the invention, the vibration generator can be placed directly below the closed base of the channel or channels, so that vibrations transmit through the thickness of the substrate through to the base of the channel and thereafter through to the fluid within the channel or channels. In this arrangement, the thickness of the substrate between the lower or underneath surface of the substrate and the base of the channel or channels might be greater than the thickness of the substrate between the lower or underneath surface and the upper surface when the vibration generator is placed on the upper surface of the substrate.

Indeed, the thickness of the substrate between the upper and lower surfaces can vary if required. In early prototypes, the thickness of the substrate between the upper and lower surfaces has been constant and in the range of 200 to 525 micrometres. In these prototypes, the substrate has been of a rectangular configuration although other configurations such as square, circular or other configuration remains within the scope of the present invention.

If the vibration generator is chosen to be a piezoelectric actuator, then any suitable form of that actuator can be employed. The piezoelectric actuator will be electrically activated or excited and this could be by mains electrical power, or more preferably, by battery power. Persons skilled in the art of the prior art nebulizers discussed herein will be familiar with suitable piezoelectric actuators and how they are set up to generate vibration.

A piezoelectric actuator can be attached to the substrate in any suitable manner such as by acoustic coupling fluids or adhesives.

As indicated above, the substrate can be a disposable substrate. In contrast, the piezoelectric actuator is preferably not disposable given it has a significant cost relative to the substrate and so the actuator preferably is transferable between substrates and so the manner of attaching the piezoelectric actuator to the substrate preferably can accommodate this.

The linear channel formed in the substrate can extend fully across the substrate from one side to the other and open through the side edges of the substrate. Alternatively, one end of the linear channel can open through one side edge of the substrate and the other and opposite end can terminate within the substrate and so have a blind end. Still alternatively, both ends of the linear channel can terminate within the substrate and so both ends can be blind.

The linear channel is fed fluid from the feeding facility. The feeding facility can have any suitable form and in one form, includes a reservoir into which fluid is fed for subsequent passage or travel into the channel. The reservoir can be formed in the substrate. The reservoir can be formed in direct communication with the channel, for example with one end of the channel. That is, the channel can open directly into the reservoir. The feeding facility can feed the reservoir from which fluid can enter the channel for atomisation. The reservoir can have any suitable shape and configuration and in some forms it has a generally circular periphery that opens through the upper surface of the substrate and is generally spherical below the upper surface. The depth of the reservoir can be about the same depth as the channel, or it can be of a greater or lesser depth.

A single reservoir can feed multiple channels so that more than one channel extends into direct communication with the reservoir. For example, a pair of intersecting channels that form a cross could be fed by a reservoir that is located at the intersection of the channels. Alternatively, multiple reservoirs can be provided to feed multiple channels.

A reservoir can be positioned at one end of a linear channel as described above, or it can be positioned elsewhere within the channel. A reservoir could be positioned centrally of a channel for example so that fluid can be fed into the channel from either side or opposite sides of the channel. Alternatively, a pair of channels that are positioned perpendicular to each other can both intersect with and thus be in direct communication with a reservoir. A pair of reservoirs can be employed with one reservoir being positioned at one end of a channel and a second reservoir positioned at the opposite end.

The feeding facility can comprise just the reservoir or reservoirs discussed above, so that in use, fluid is delivered into the reservoir or reservoirs and thereafter the nebulizer of the invention can be operated to atomise the fluid. Atomisation can continue until all of the fluid is atomised or until a satisfactory amount of fluid has been atomised. Where the substrate of the nebulizer is disposable, any excess fluid can be disposed of as well, or where the substrate of the nebulizer is to be cleaned or sterilized, any excess fluid will be removed in that process.

However, the feeding facility can include further structure and can for example include a feed conduit or tube that facilitates feed of fluid into the reservoir or reservoirs. Alternatively, the feeding facility can include a feed conduit or tube that facilitates feed of fluid directly into the channel or channels, so that a reservoir formed in the substrate is not required. In this form of the invention, the feeding facility can still include a reservoir, but the reservoir is not formed in the substrate, but is separate from the substrate. In this latter respect, the reservoir can be an external reservoir and for example, such a reservoir could be in the form of a container such as a blister pack or the like. Another form of external reservoir could be a vial. In each case, the blister pack or vial could already be filled with a fluid to be atomised and can be connected directly or indirectly to the channel. A suitable connection to connect between the blister pack or vial and the nebulizer can form part of the nebulizer.

Alternatively, the feeding facility can include a wicking arrangement to wick fluid from a reservoir or fluid supply, which is either part of the substrate or is separate from the substrate.

The feeding facility can be set up so that a particular dose of a particular fluid can be delivered or made available to the channel or channels. Alternatively, the arrangement can be such that once the reservoir or the channel is filled appropriately, further feed terminates. The feeding facility can be arranged to be self-replenishing so that upon fluid in the channel or reservoir being exhausted, or reduced to a certain level, the feeding facility can replenish the channel or reservoir. Alternatively, the feeding facility can be arranged to replenish the channel or reservoir constantly as fluid in the channel is atomised so that the level of fluid in the channel or reservoir remains generally constant. The feeding facility can thus also remove the need for residual fluid that is not atomised to be recycled. This is a significant benefit.

The entry or passage of fluid into the channel or channels can be by any suitable mechanism, and advantageously, capillary action or flow can be employed. Thus, in some forms of the invention, a reservoir can supply a channel by capillary action, so that as fluid within the channel is atomised and drawn out of the channel, fluid within the reservoir flows into the channel automatically and without external input, such as by pumping. This arrangement can be used provide an atomised dosage, by the reservoir including a set amount of fluid representing a single dose and the fluid flowing under capillary action into the channel from the reservoir until the fluid within the reservoir is exhausted or is reduced to a level at which capillary flow ceases or terminates.

Nebulizers according to the invention can operate with low heat waste as the liquid medium is separated from and therefore not in contact with the vibration generator, usually a piezoelectric actuator. Nebulizers according to the invention have a channel spaced from the vibration generator and fluid is drawn into the channel from a feeding facility. Early prototypes of the invention have advantageously atomised highly monodisperse micro droplets with diameters ranging from 4.3 to 6.5 micrometres with a size variation of about 0.25 micrometres. The stable nature of the invention and the ability to provide consistent fluid feed means that the droplet size produced can be tuned or specified and consistently provided.

The components of the nebulizer described above are housed within a housing to form the nebulizer. The housing defines a chamber within which atomised droplets or fluid particles accumulate while the outlet of the chamber allows for a user of the nebulizer to draw the atomised droplets out of the chamber, such as for inhalation. The outlet can be appropriately shaped and sized for inhalation purposes or it can be arranged for the attachment of an inhalation device, such as a mouthpiece.

Where the invention is used for non-medical applications, such as for thin film deposition or mass spectrometry, the housing can be different, or it can be omitted entirely. Thus, for those uses, the invention can provide a nebulizer having:
 a. a solid substrate,
 b. a linear channel formed in the substrate that has a closed base, opposite side walls and an opening that opens through an upper surface of the substrate,
 c. a vibration generator attached to the substrate at a position spaced from the channel for generating high frequency vibration that transmits through the substrate to the channel to atomise fluid within the channel, and
 d. a feeding facility for feeding fluid to the channel.

In the above form of the invention, the atomised fluid is not captured within the chamber of a housing, but rather, is otherwise captured or directed as required. A nebulizer according to this form of the invention can have all of the features described above in relation to the earlier form of the invention in which a housing is provided.

In a nebulizer according to the invention, the atomised droplet size can be tuned by modifying channel geometry, and actuation frequency and amplitude. A key advantage of the present invention is the ability to alter the design of the substrate, including the dimensions and geometry of the channel or channels and the spacing of the vibration generator from the channel or channels, which would be able to provide different types of droplets (in term of physical size and chemical composition). Different channel design and surface modification are important to this advantage. Unlike other commercially available nebulizers, especially in comparison to vibrating mesh nebulizers, the present invention will enable users to easily change the substrate and thus change the characteristics of the atomized fluid. That is, both the structure of a channel of the substrate and the location of the vibration generator relative to a channel of the substrate can be changed by changing the substrate of the nebulizer.

The invention advantageously provides a simple and cheap nebulizer for the generation of highly monodispersed aerosol particles.

BRIEF DESCRIPTION OF DRAWINGS

In order that the invention may be more fully understood, some embodiments will now be described with reference to the figures in which.

DETAILED DESCRIPTION

Figure 1:
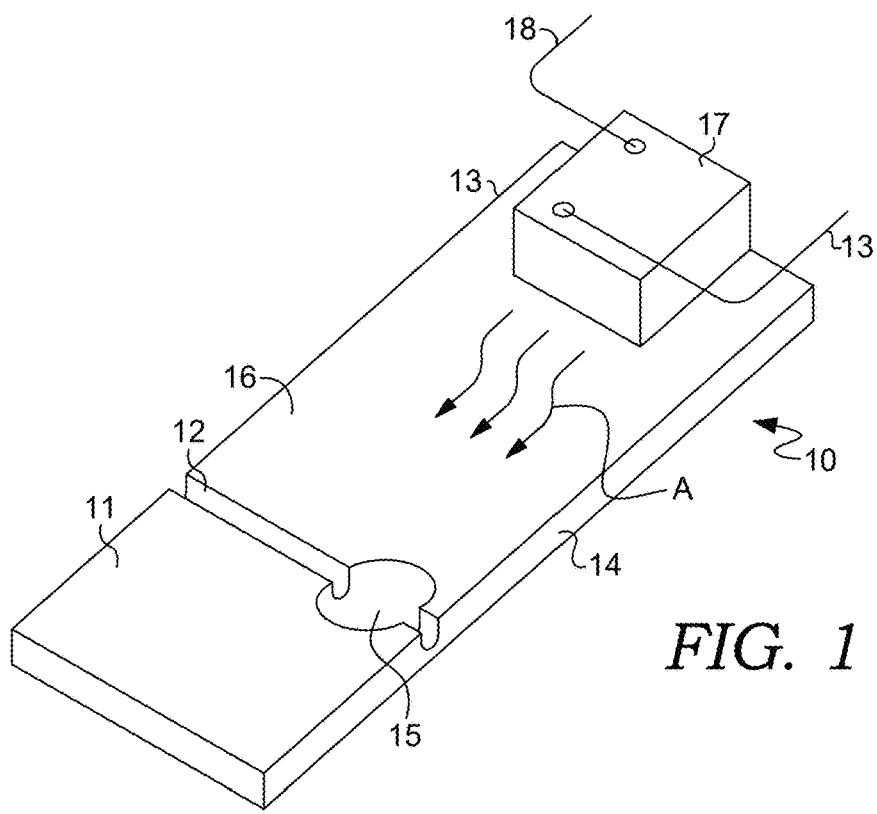
FIG. 1 is a perspective view of a nebulizer according to one embodiment of the invention.

FIG. 1 illustrates a nebulizer 10 according to one embodiment of the present invention. The nebulizer 10 is shown without a housing being depicted, so that the features of the nebulizer 10 can be easily shown. Accordingly, the nebulizer 10 of FIG. 1 is formed from a substrate 11 that is rectangular in configuration and includes a linear channel 12 that extends laterally across the substrate 11 between respective long sides 13 and 14 of the substrate 11. It can be seen that the channel 12 extends through the long side 13 at one end, and extends into a generally circular reservoir 15 at the other end. The channel 12 extends for a short extent on the opposite side of the reservoir 15 to extend through the opposite long side 14. The channel 12 includes a closed base and opposite side walls and an opening that opens through the upper surface 16 of the substrate 11. The dimensions of the channel 12 are greatly exaggerated in FIG. 1 for the purpose of illustration. As will be appreciated from the discussion earlier herein, the opening of the channel 12 through the upper surface 16 of the substrate 11 can have a width transverse to the length from about 1.5 micrometres to about 20 micrometres. The depth of the channel can be from about 10.5 micrometres up to about 300 micrometres.

A vibration generator 17 is mounted on the upper surface 16 of the substrate 11 at a position spaced from the channel 12 and is in the form of a piezoelectric actuator. The piezoelectric actuator is a piezoelectric block. The actuator 17 is connected in a normal manner to cables 18 that attach to separate electrodes of the actuator 17 and that supply electric current to the actuator 17 for the purpose of exciting the actuator 17. Upon the actuator 17 being excited, high frequency vibrations are generated that transmit through the substrate 11 in the direction towards the channel 12 as shown by the arrows A. The vibrations reach the channel 12 and cause atomisation of fluid within the channel 12.

Figure 2:
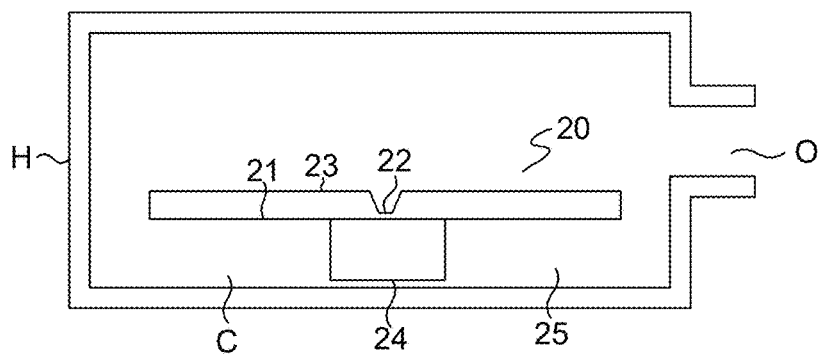
FIG. 2 is a side view of a nebulizer according to another embodiment of the invention.
Figure 5:
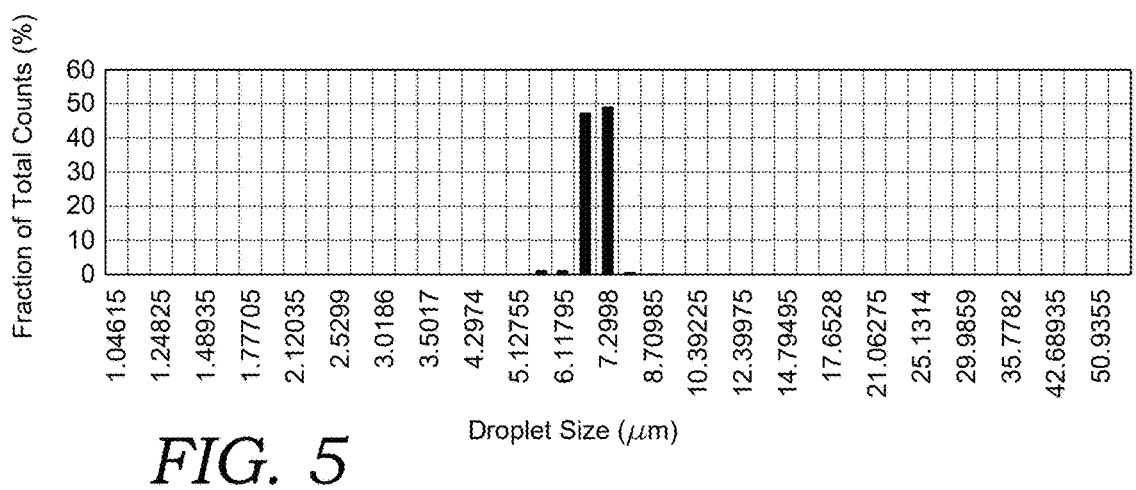
FIG. 5 graphically illustrates the typical size distribution of droplets for a 20 μm wide, 200 μm deep channel in a substrate that is excited at 675 KHz.
Figure 3:
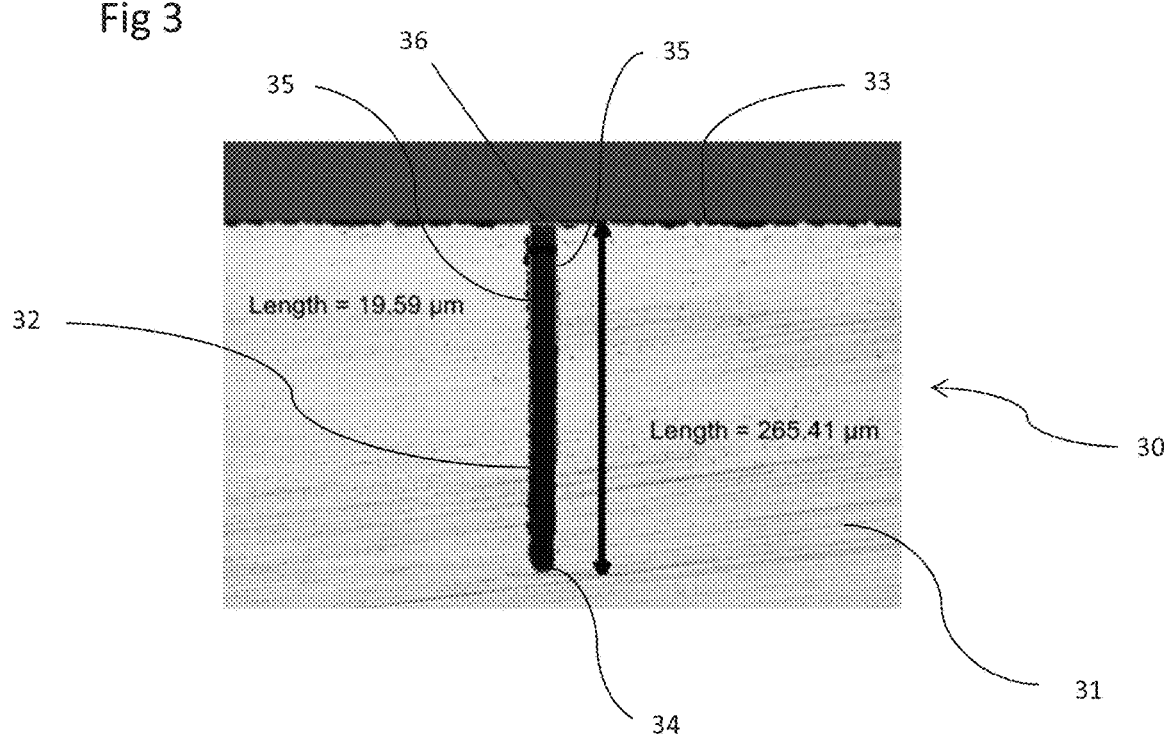
FIG. 3 is a photograph in cross-sectional side view of a prototype nebulizer according to the invention.
Figure 4:
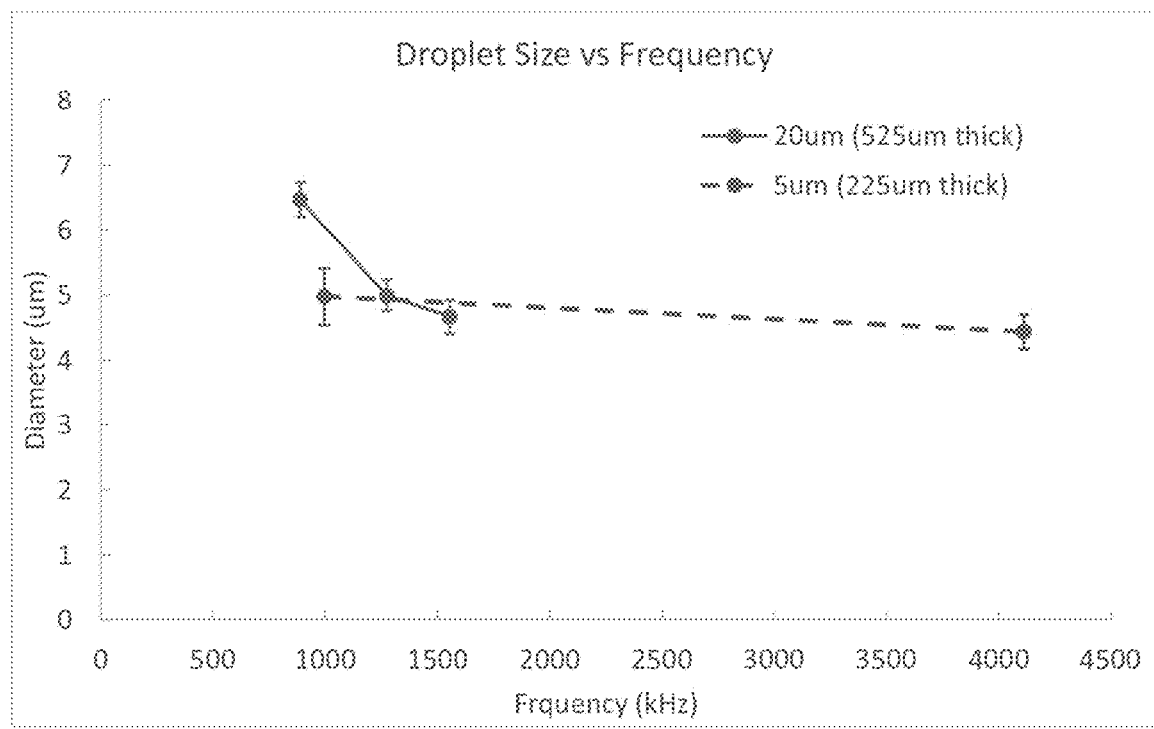
FIG. 4 is a graph created from prototype testing in relation to nebulizers according to the invention that are excited at different frequencies.
Figure 6:
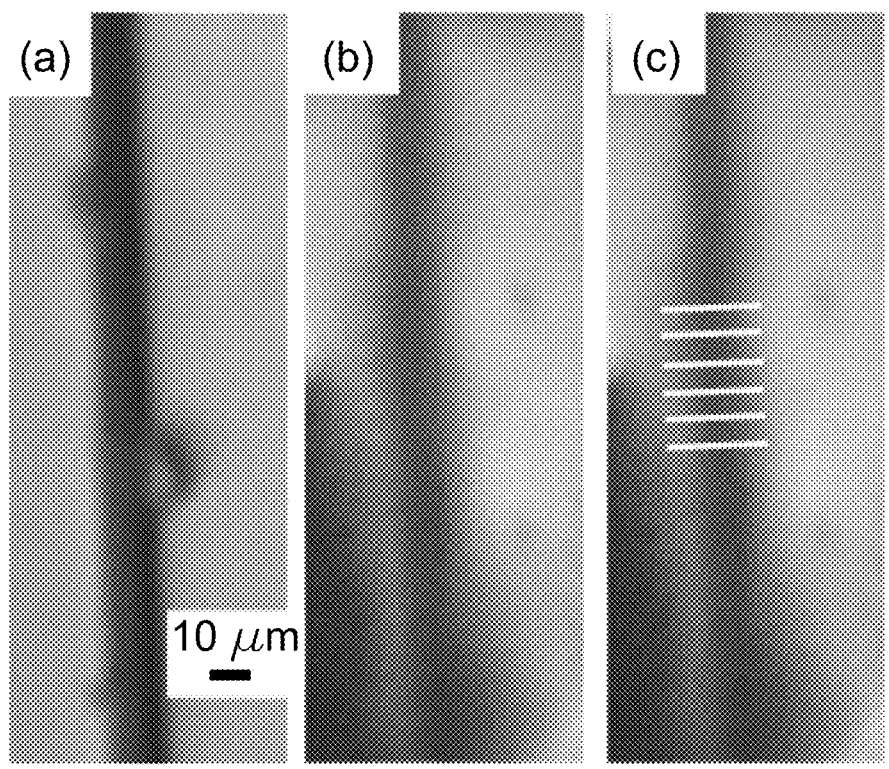
FIGS. 6(a) to 6(c) are a series of still images taken from high speed imagery looking down on 13.75 μm wide channels etched into a a silicon wafer during nebulisation.

FIG. 2 illustrates an alternative arrangement of a nebulizer 20 according to another embodiment of the present invention. The nebulizer 20 is shown housed within a housing H. The housing H defines a chamber C within which atomised droplets or fluid particles accumulate and the chamber C includes an outlet O that allows for a user of the nebulizer to draw the atomised droplets out of the chamber C, such as for inhalation. The nebulizer of FIG. 2 is shown from the side and includes a square or rectangular substrate 21 and linear channel 22 that extends laterally across the substrate 21. The channel 22 is fed by a generally circular reservoir which is not shown, but which can be assumed to be the same as or similar to the reservoir 15 of FIG. 1. Thus, the channel 22 extends through opposite sides of the substrate 21. The channel 22 includes a closed base and opposite side walls and an opening that opens through the upper surface 23 of the substrate 21. The dimensions of the channel 22 are greatly exaggerated in FIG. 2 as they were in FIG. 1 for the purpose of illustration.

A vibration generator 24 is mounted on the lower or underneath surface 25 of the substrate 21 at a position spaced from the closed base of the channel 22. The vibration generator 24 is again in the form of a piezoelectric actuator. The actuator 24 is connected in a normal manner to cables (not shown) that supply electric current to the actuator 24 for the purpose of exciting the actuator 24. Upon the actuator 24 being excited, high frequency vibrations are generated that transmit through the substrate 21 in the direction towards the channel 22. Obviously the distance shown for the vibrations to travel to reach the channel 22 is much shorter than illustrated in FIG. 1, but the thickness of the substrate 21 can be selected to provide an appropriate distance for vibration propagation. In the same manner as FIG. 1, the vibrations reach the channel 22 and cause atomisation of fluid within the channel 22.

The vibration generator 24 is placed directly below the closed base of the channel 22. In alternative arrangements, the vibration generator 24 can be offset from the channel 22 but still located on the underneath surface 25 of the substrate 21.

FIG. 3 is a photograph taken with a microscope and illustrates an actual prototype nebulizer according to the invention which is shown in side cross-section. The nebulizer 30 has a substrate 31, a channel 32 and an upper surface 33. The dark section above the surface 33 is background and is not part of the nebulizer 30. The channel 32 has a closed base 34, opposite side walls 35 that are generally parallel and a lateral opening 36 that opens through the upper surface 33. The substrate 31 is a silicon wafer and the channel 32 is formed by deep reactive ion etching. The internal surface of the channel 32 has been rendered hydrophilic by the use of the application of $O_2$ plasma.

The dimensions of the channel 32 are given in FIG. 3. Thus, the transverse width of the channel 32 is 19.59 μm, while the length or height of the channel 32 extending downwardly from the upper surface 33 to the close base 34, is 265.41 μm. These measurements will give context to the nebulizers 10 and 20 illustrated in FIGS. 1 and 2, in terms of dimensional size.

FIG. 4 is a graph created from prototype testing in relation to nebulizers according to the invention that are excited at different frequencies. The Y-axis gives the diameter in μm of the droplet size that is produced, while the X-axis gives the vibration frequency that is applied to the substrate by the vibration generator. The graph shows that a range of the droplet sizes are produced at a particular frequency, The graph also illustrates the use of two different sized channels and substrate thicknesses, whereby the channel dimensions given is the lateral opening dimension of the channels through the upper surface of the substrate in which the channels are formed and the substrate dimension is the thickness of the substrate between the upper and lower surfaces of the substrate. Thus, the results relate to different channels having respective lateral openings of 20 μm and 5 μm and substrate thicknesses of 525 μm and 225 μm.

The graph shows that there is a highly advantageous result produced by the present invention. The graph for the 20 μm channel shows that the droplet size does not vary greatly at a particular frequency. For the 20 μm channel, at each of the approximate 1 MHz, 1.3 MHz and 1.6 MHz points, the extent to which there is variation in droplet size is approximately the same and within the range of about 0.5 μm. For the 5 μm channel, at each of the approximate 1 MHz and 4.15 MHz points, the variation in droplet size is approximately between 0.5 μm and 0.9 μm. That level of variability is very low and the consistency is very good.

This result is that the mean diameters of the droplets that are produced by a nebulizer according to the present invention, can be maintained within a small range of different sizes. Thus, the particles are generally of the same size. This differs from nebulizers according to the prior art, in which there is much greater variation in the diameter of droplets produced. Thus, the present invention provides high levels of control over the mean diameter of the droplets produced. This is highly advantageous for aerosol drug delivery into the lungs, as the size of delivered droplets determines where in the lung the droplets are deposited as well as influencing the therapeutic effectiveness of the drug. As shown in FIG. 4, the size of the particles can be tuned on-demand by changing the frequency of actuation.

As previously described, from measurements of the droplet size relative to the driving frequency of the high frequency vibration, as well as imagery that has been observed of the fluid/air interface, capillary waves form at the fluid/air interface at the opening of a channel formed in the substrate. The use of a vibration generator such as a piezoelectric actuator which is capable of exciting a substrate at a range of frequencies, different sizes of droplets can be produced from the same nebulizer. Physical properties affecting capillary wavelength at the fluid/air interface include 1) the density of the two fluids in contact, 2) the surface tension and 3) the driving wavelength. FIG. 5 graphically illustrates the typical size distribution of droplets for a 20 μm wide, 200 μm deep channel in a substrate that is excited at 675 KHz.

FIGS. 6(a) to 6(c) is a series of still images taken from high speed imagery looking down on 13.75 μm wide channels etched into a silicon wafer during nebulisation. FIG. 6(a) shows a water filled channel with no frequency generation. No capillary waves are apparent on the surface of the water. In FIG. 6(b), a 675 KHz frequency generation has been applied to the substrate, creating capillary waves on surface of the water. In FIG. 6(c) the wavelength of the capillary waves of FIG. 6(b) are shown, and these have been measured to be approximately 9.5 μm.

Figure 7:
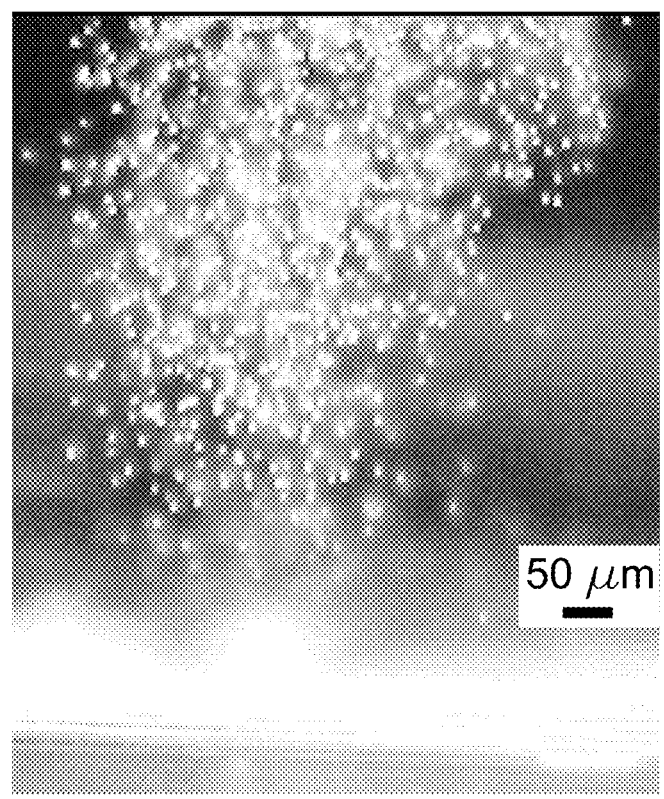
FIG. 7 is a still image of the atomized droplets produced in a nebulizer that has a channel that is 20 μm wide and 200 μm deep that is excited at 675 KHz.

FIG. 7 is a still image of the atomized droplets produced in a nebulizer that has a channel that is 20 μm wide and 200 μm deep that is excited at 675 KHz. The nebulizer produces droplets approximately 7 m in diameter. High speed imagery used to measure these droplets detected a droplet velocity about 0.6-1 m·s−1 vertically.

Where any or all of the terms "comprise", "comprises", "comprised" or "comprising" are used in this specification (including the claims) they are to be interpreted as specifying the presence of the stated features, integers, steps or components, but not precluding the presence of one or more other features, integers, steps or components.

Those skilled in the art will appreciate that the invention described herein is susceptible to variations and modifications other than those specifically described. It is understood that the invention includes all such variations and modifications which fall within the spirit and scope of the present invention.

The invention claimed is:

1. A nebulizer comprising:
- a housing,
- the housing defining a chamber and having an outlet to the chamber for the egress of atomised fluid particles from within the chamber,
- a solid substrate within the chamber of the housing,
- a linear channel formed in the substrate that has a closed base, opposite side walls and an opening that opens through an upper surface of the substrate,
- a vibration generator attached to the substrate at a position spaced from the linear channel for generating high frequency vibration that transmits through the substrate to the channel to atomise fluid within the linear channel, and
- a feeding facility for feeding fluid to the linear channel,
- wherein the linear channel has a high aspect ratio which the depth of the channel is greater than the width, the depth of the channel is in the range of 10.5 micrometres when a linear channel has an aspect ratio of 7:1 and a channel opening of 1.5 micrometres and, up to a 300 micrometers when a channel has aspect ratio of 15:1 and a channel opening of 20 micrometres, and
- wherein the linear channel extends fully across the substrate and opens through side edges of the substrate.

2. The nebulizer according to claim 1, wherein the substrate is a rigid substrate, in particular being formed from silicon.

3. The nebulizer according to claim 1, wherein the surface of the linear channel is treated to render the surface of the linear channel hydrophilic.

4. The nebulizer according to claim 3, wherein the surface of the linear channel is treated to render the surface of the linear channel hydrophilic by the application of $O_2$ plasma to the channel surface.

5. The nebulizer according to claim 1, wherein the nebulizer includes multiple linear channels that are formed in a parallel array or perpendicular to each other, or in a T or L formation for two channels, or in a C or square/rectangular formation for three or four linear channels.

6. The nebulizer according to claim 1, wherein the vibration generator is a piezoelectric actuator that employs a piezoelectric disc that is actuated or excited electrically.

7. The nebulizer according to claim 6, wherein the piezoelectric actuator generates actuation vibrations in a frequency range from 500 KHz to 5 MHz or from 5 MHz to 20 MHz.

8. The nebulizer according to claim 1, wherein the vibration generator is placed on the upper surface of the substrate.

9. The nebulizer according to claim 1, wherein the vibration generator is placed on a lower or underneath surface of the substrate opposite to the upper surface through which the linear channel opens.

10. The nebulizer according to claim 9, wherein the vibration generator is placed directly below the closed base of the linear channel.

11. The nebulizer according to claim 1, wherein both ends of the linear channel terminate within the substrate.

12. The nebulizer according to claim 1, wherein the feeding facility has a reservoir into which fluid is fed for subsequent passage or travel into the linear channel.

13. The nebulizer according to claim 12, wherein the reservoir is formed in the substrate.

14. The nebulizer according to claim 1, wherein the feeding facility includes a feed conduit or tube that facilitates feed of fluid directly into the linear channel.

15. The nebulizer according to claim 1, wherein the feeding facility includes an external reservoir spaced from the substrate.

16. A nebulizer comprising:
- a housing,
- the housing defining a chamber and having an outlet to the chamber for the egress of atomised fluid particles from within the chamber,
- a solid substrate within the chamber of the housing,
- a linear channel formed in the substrate that has a closed base, opposite side walls and an opening that opens through an upper surface of the substrate,
- a vibration generator attached to the substrate at a position spaced from the linear channel for generating high frequency vibration that transmits through the substrate to the channel to atomise fluid within the linear channel, and
- a feeding facility for feeding fluid to the linear channel,
- wherein the linear channel has a high aspect ratio in which the depth of the channel is greater than the width, the depth of the channel is in the range of 10.5 micrometres when a linear channel has an aspect ratio of 7:1 and a channel opening of 1.5 micrometres and, up to a 300 micrometers when a channel has aspect ratio of 15:1 and a channel opening of 20 micrometres, and
- wherein one end of the linear channel opens through one side edge of the substrate and an opposite end of the linear channel terminates within the substrate.

17. A nebulizer comprising:
- a solid substrate,
- a linear channel formed in the substrate that has a closed base, opposite side walls and an opening that opens through an upper surface of the substrate,
- a vibration generator attached to the substrate at a position spaced from the linear channel for generating high frequency vibration that transmits through the substrate to the linear channel to atomise fluid within the linear channel, and a feeding facility for feeding the fluid to the linear channel, wherein the linear channel has a high aspect ratio in which the depth of the channel is greater than the width, the depth of the channel is in the range of 10.5 micrometres when a linear channel has an aspect ratio of 7:1 and a channel opening of 1.5 micrometres and, up to a 300 micrometre when a channel has aspect ratio of 15:1 and a channel opening of 20 micrometres, and wherein the linear channel extends fully across the substrate and opens through side edges of the substrate.

18. A nebulizer comprising:

a solid substrate, a linear channel formed in the substrate that has a closed base, opposite side walls and an opening that opens through an upper surface of the substrate, a vibration generator attached to the substrate at a position spaced from the linear channel for generating high frequency vibration that transmits through the substrate to the linear channel to atomise fluid within the linear channel, and a feeding facility for feeding the fluid to the linear channel, wherein the linear channel has a high aspect ratio in which the depth of the channel is greater than the width, the depth of the channel is in the range of 10.5 micrometres when a linear channel has an aspect ratio of 7:1 and a channel opening of 1.5 micrometres and, up to a 300 micrometre when a channel has aspect ratio of 15:1 and a channel opening of 20 micrometres, and wherein one end of the linear channel opens through one side edge of the substrate and an opposite end of the linear channel terminates within the substrate.

\* \* \* \* \*